(12) United States Patent
Theuveny et al.

(10) Patent No.: US 11,796,362 B2
(45) Date of Patent: Oct. 24, 2023

(54) CONDUCTIVITY PROBE FLUID PROPERTY MEASUREMENT SYSTEMS AND RELATED METHODS

(71) Applicant: Schlumberger Technology Corporation, Sugar Land, TX (US)

(72) Inventors: Bertrand Theuveny, Clamart (FR); Ryan Donald Williams, Houston, TX (US); Cheng-Gang Xie, Singapore (SG); Guillaume Jolivet, Singapore (SG)

(73) Assignee: Schlumberger Technology Corporation, Sugar Land, TX (US)

( * ) Notice: Subject to any disclaimer, the term of this patent is extended or adjusted under 35 U.S.C. 154(b) by 382 days.

(21) Appl. No.: 16/490,616

(22) PCT Filed: Mar. 2, 2018

(86) PCT No.: PCT/US2018/020590
§ 371 (c)(1),
(2) Date: Sep. 3, 2019

(87) PCT Pub. No.: WO2018/160927
PCT Pub. Date: Sep. 7, 2018

(65) Prior Publication Data
US 2020/0003599 A1 Jan. 2, 2020

Related U.S. Application Data
(60) Provisional application No. 62/466,607, filed on Mar. 3, 2017.

(51) Int. Cl.
*G01F 1/74* (2006.01)
*G01F 15/02* (2006.01)
(Continued)

(52) U.S. Cl.
CPC .............. *G01F 1/74* (2013.01); *G01F 15/022* (2013.01); *G01N 27/08* (2013.01); *G01N 33/2823* (2013.01)

(58) Field of Classification Search
CPC ............ G01F 1/74; G01F 15/022; G01F 3/00; G01N 27/08; G01N 33/2823
(Continued)

(56) References Cited

U.S. PATENT DOCUMENTS 5,594,179 A * 1/1997 Marsh .................... G01F 1/704
73/861.05
6,831,470 B2 12/2004 Xie et al.
(Continued)

FOREIGN PATENT DOCUMENTS

CA 2300794 A1 * 11/2000 .......... G01F 1/7088
CN 101738226 A 6/2010
(Continued)

OTHER PUBLICATIONS

English translation of CN 106496528, Mar. 2017 (Year: 2017).*
(Continued)

*Primary Examiner* — Michael P Nghiem
(74) *Attorney, Agent, or Firm* — Jeffrey D. Frantz

(57) ABSTRACT

Conductivity probe fluid property measurement systems and related methods are disclosed herein. An example apparatus includes a flow meter and a fluid conduit to provide a flow path for a fluid relative to the flow meter. The example apparatus includes a conductivity probe coupled to the fluid conduit to generate brine conductivity data of the fluid during flow of the fluid through the fluid conduit. The example apparatus includes a processor to modify fluid flow data generated by the flow meter based on the brine conductivity data.

19 Claims, 9 Drawing Sheets

(51) Int. Cl.
*G01N 27/08* (2006.01)
*G01N 33/28* (2006.01)

(58) Field of Classification Search
USPC .......................................................... 702/45
See application file for complete search history.

(56) References Cited

U.S. PATENT DOCUMENTS

| | | |
|---|---|---|
| 9,528,869 B2 | 12/2016 | Xie et al. |
| 2009/0088985 A1 | 4/2009 | Wee |
| 2010/0196244 A1* | 8/2010 | Grauer ..................... C01D 7/18 |
| | | 422/187 |
| 2013/0153210 A1* | 6/2013 | Menard ............... E21B 43/2408 |
| | | 166/57 |
| 2013/0327154 A1 | 12/2013 | Xie et al. |
| 2014/0020462 A1 | 1/2014 | Irani et al. |
| 2016/0011032 A1* | 1/2016 | Hogendoorn ............. G01F 1/74 |
| | | 324/306 |
| 2016/0011033 A1 | 1/2016 | Chen et al. |
| 2016/0024909 A1* | 1/2016 | Han ........................ E21B 47/11 |
| | | 166/250.1 |
| 2016/0169720 A1 | 6/2016 | Xie et al. |
| 2016/0169726 A1 | 6/2016 | Xie et al. |
| 2018/0016897 A1* | 1/2018 | Willberg ................. E21B 41/00 |
| 2019/0186246 A1* | 6/2019 | Reed ........................ H04B 3/54 |
| 2020/0033174 A1* | 1/2020 | Nogueira ................. G01F 1/86 |

FOREIGN PATENT DOCUMENTS

| | | | |
|---|---|---|---|
| CN | 101786056 A | 7/2010 | |
| CN | 104374441 A | 2/2015 | |
| CN | 106496528 * | 3/2017 | |
| DE | 102006037739 A1 | 2/2007 | |
| EP | 2251433 A2 * | 11/2010 | ............. C12Q 1/001 |
| GB | 2529538 A * | 2/2016 | ........... G01N 27/025 |
| WO | 2015019081 A1 | 2/2015 | |
| WO | 2015142610 A1 | 9/2015 | |
| WO | WO-2016142541 A1 * | 9/2016 | ........... E21B 47/001 |

OTHER PUBLICATIONS

International Preliminary Report on Patentability issued in the related PCT Application PCT/US2018/020590, dated Sep. 12, 2019 (10 pages).
International Search Report and Written Opinion issued in the related PCT Application PCT/US2018/020590, dated Jun. 8, 2018 (13 pages).
First Office Action of Chinese Patent Application No. 2021101801881630 dated Oct. 21, 2021, 23 pages with English translation.
Second Office Action of Chinese Patent Application No. 2021101801881630 dated Aug. 3, 2022, 21 pages with English translation.

* cited by examiner

CONDUCTIVITY PROBE FLUID PROPERTY MEASUREMENT SYSTEMS AND RELATED METHODS

RELATED APPLICATION

This patent claims the benefit of U.S. Provisional Patent Application No. 62/466,607, which was filed on Mar. 3, 2017. U.S. Provisional Patent Application No. 62/466,607 is hereby incorporated by reference in its entirety. Priority to U.S. Provisional Patent Application No. 62/466,607 is hereby claimed.

BACKGROUND

Field of the Disclosure

This disclosure relates generally to determining fluid properties using a conductivity probe. In particular, this disclosure relates to systems and methods for determining fluid properties in real-time or substantially real-time for monitoring and control of, for instance, various industrial, oil and gas exploration, and mining operations.

Description of the Related Art

Conductivity probes or systems are sometimes used to measure the conductivity of water contained in oil/water/gas multiphase flows. The water conductivity measurement may then be used to infer changes in water salinity or to track changes in calibration of the water mass-attenuation coefficient provided to a multiphase flow meter (MPFM), such as a gamma-ray fraction meter.

Additionally, in oil and gas exploration and production, fracturing in shale environments may utilize a MPFM to provide monitoring of the fracturing process during various types of fracturing operations, such as a Frac Plug Drill-Out (FPDO) and flowback operations. FIG. 1 shows a known system 100 including a MPFM 102 that may be used to monitor flow of fluid from a reservoir being fractured. The MPFM 102 of FIG. 1 measures individual-phase flow rates of well fluids (e.g., gas, oil and water) during FPDO and flowback operations as a fluid flows between an inlet 104 and an outlet 106 of a fluid conduit 107. The MPFM 102 of FIG. 1 is typically deployed, post frac pumping, upstream of the choke or, in some examples, upstream of sand traps to enable monitoring of sands and/or solids. As represented by block 108 of FIG. 1, samples of water are collected manually to ensure that the MPFM 102 makes correct flow rate measurements in FPDO operations where water salinity often varies. A series of post job in-situ calibrations for the water are performed to modify the MPFM data, such as gamma-ray water attenuations, as represented by block 110 of FIG. 1. The calibrations are provided to a data processor 112 that is in communication with the MPFM 102 and that generates one or more outputs based on fluid flow data generated by the MPFM 102. In particular, the calibrations from the manual sampling analysis are provided to the data processor 112 to enable the data processor 112 to generate individual-phase flow-rate computations (e.g., gas flow rate, oil flow rate, water flow rate) determined based on the data collected by the MPFM 102 that account for changes in salinity. The consequences of not correcting for changes in salinity include incorrect estimates of the flow rates of oil and/or condensate and misinterpretations of the changes in salinity as production of solids/sand.

Moreover, a MPFM engineer is usually not present for the whole duration of the operation when fracturing fluids delivery and flowback services are operating. The engineer may be present for the rig-up or during the first few hours of flow and may also manage other tools at the job site. A typical FPDO operation, however, lasts for few days while a typical subsequent flowback operation lasts for 3 days to 3 months. One of the main challenges today in the MPFM data post-processing is the lack of interpolation capability to ensure a continuous adjustment of changes of water properties. The event-centered changes of water-attenuations may generate undesirable step changes to the flow-rate computations, which create challenges to accuracy in, for example, estimating flow rates, and misunderstandings by operators. Accordingly, it would be desirable to provide the MPFM post-processing analysis with continuously measured brine salinity data.

Referring again to the known system 100 of FIG. 1, the challenge without a conductivity probe to, for example, track water conductivity/salinity variation is that the water properties change rapidly, particularly during FPDO and in the early phase of flowback operations. For example, water salinity may change from fresh water to having a salt concentration of 100,000 ppm in a matter of hours. Additionally, fracture well bores can inadvertently be compromised if the fracking operations stray outside the operating envelope, thereby severely limiting and, in some cases, damaging the reservoir fracture connectivity and productivity. Thus, there is a need for improved monitoring and control of well reservoir fluids that may fluctuate during various operations.

SUMMARY

Some examples disclosed herein include systems and methods for monitoring and controlling conventional and unconventional wells, pipes, or streams during oil and gas exploration and production.

Some examples disclosed herein include systems and methods for monitoring and controlling operations in other industries, such as mining, monitoring and analysis of industrial waste streams, and evaluation and control of water quality in aquifers and surface waters.

Some examples disclosed herein include systems and methods for using a conductivity probe in applications with multiphase fluids in the presence of solids, such as measuring the water conductivity variation, improving the detection of solids and/or slugs, and identifying reservoir properties, such as connected fracture chemistry/geometry in unconventional shale well FPDO and flowback operations.

An example apparatus disclosed herein includes a flow meter and a fluid conduit to provide a flow path for a fluid relative to the flow meter. The example apparatus includes a conductivity probe coupled to the fluid conduit to generate brine conductivity data of the fluid during flow of the fluid through the fluid conduit. The example apparatus includes a processor to modify fluid flow data generated by the flow meter based on the brine conductivity data.

An example method disclosed herein includes accessing, by executing an instruction with a processor, brine conductivity data generated by a conductivity probe during flow of a multiphase fluid through a fluid conduit; accessing, by executing an instruction with the processor, fluid flow data generated by a flow meter for the multiphase fluid during the flow of the multiphase fluid through the fluid conduit; applying, by executing an instruction with the processor, a correction to the fluid flow data to generate corrected fluid flow data; and determining, by, executing an instruction with the processor, one or more of a holdup or a flow rate of a phase of the multiphase fluid based on the corrected fluid flow data.

Another example apparatus disclosed herein includes means for generating fluid flow data during flow of a fluid through a conduit; means for generating brine conductivity data for the fluid during the flow of the fluid through the conduit; and means for correcting the fluid flow data based on the brine conductivity data.

BRIEF DESCRIPTION OF THE DRAWINGS

Certain embodiments of the disclosure will hereafter be described with reference to the drawings, wherein like reference numerals denote like elements. It should be understood, however, that the accompanying drawings illustrate only the various implementations described herein and are not meant to limit the scope of various technologies described herein. The drawings show and describe various embodiments of the current disclosure.

The figures are not to scale. Instead, the thickness of the layers or regions may be enlarged in the drawings. In general, the same reference numbers will be used throughout the drawing(s) and accompanying written description to refer to the same or like parts.

DETAILED DESCRIPTION

Figure 1:
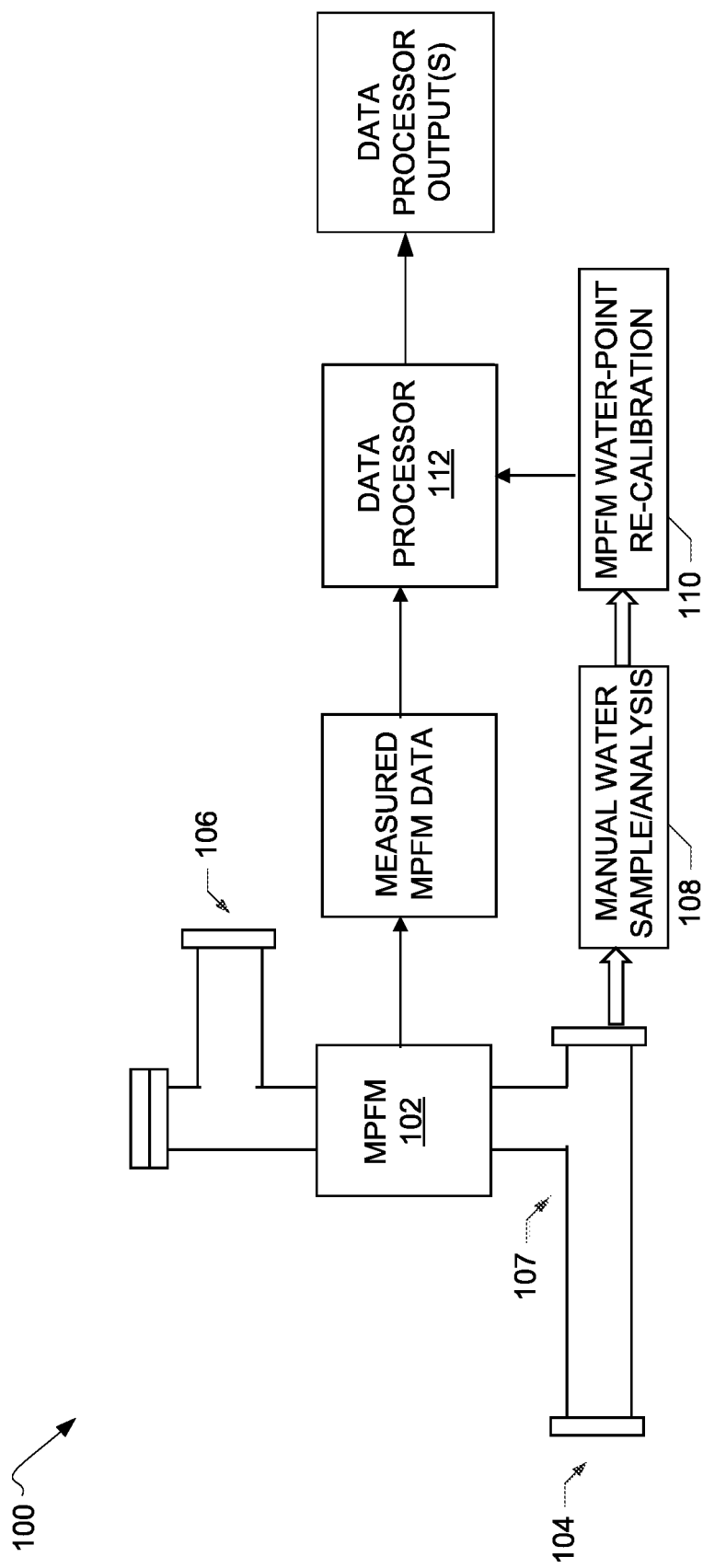
FIG. 1 is a schematic drawing of a system known in the prior art including a multiphase flow meter (MPFM) for measuring flow rates during Frac Plug Drill-Out (FPDO) and/or flowback operations.

In the following description, numerous details are set forth to provide an understanding of the present disclosure. It will be understood by those skilled in the art, however, that the embodiments of the present disclosure may be practiced without these details and that numerous variations or modifications from the described embodiments may be possible.

In the specification and appended claims: the terms "connect," "connection," "connected," "in connection with," and "connecting" are used to mean "in direct connection with" or "in connection with via one or more elements;" and the term "set" is used to mean "one element" or "more than one element". Further, the terms "couple," "coupling," "coupled," "coupled together," and "coupled with" are used to mean "directly coupled together" or "coupled together via one or more elements". As used herein, the terms "up" and "down," "upper" and "lower," "upwardly" and downwardly," "upstream" and "downstream," "above" and "below," and other like terms indicating relative positions above or below a given point or element are used in this description to more clearly describe some embodiments of the disclosure.

This present disclosures includes the use of a conductivity probe to perform real-time or substantially real-time measurement of the conductivity of water contained in a single-phase or multiphase fluid in changing environment(s) in oil and gas field operations. The conductivity probe can be used in, for instance, producing wells, injector wells, or in wells being drilled, fractured, or in the process of being abandoned. Example systems and methods disclosed herein may be used either alone or in conjunction with other devices such as (but not limited to) pressure and temperature gauges, multiphase or single phase flow meters, instrumented separators, sand measurement devices located upstream and/or downstream of the conductivity probe, ion-selective electrodes, and pH sensors. Example systems and methods disclosed herein may also be used with an automated or manual sampling system.

Example systems and methods disclosed herein may be used in other applications, such as monitoring and controlling operations in other industries, such as mining, monitoring and analysis of industrial waste streams, and evaluation and control of water quality in aquifers and surface waters. For example purposes, however, the systems and methods disclosed herein will be discussed in the context of fracturing operations used in oil and gas exploration and production.

Example systems and methods disclosed herein provide for monitoring, controlling, and characterizing fluid from fracking operations using a MPFM in conjunction with a conductivity probe. Example systems and methods disclosed herein may be used alone or in conjunction with other devices such as (but not limited to) pressure and temperature gauges, multiphase or single phase flow meters, instrumented separators, sand measurement devices located upstream and/or downstream of the conductivity probe, ion-selective electrodes, and pH sensors. Example systems and method disclosed herein can also be used with an automated sampling system and/or a manual sampling system.

In examples disclosed herein, the fluid being characterized can be monophasic or multiphasic (i.e., where the phases can be any of the combinations of water, oil, gas, solids (including undissolved salts), mud and slurries, steam, or cement). In examples in which the fluid is multiphasic, the multiphase fluid can have forms such as segregated flow, emulsion, foam, and doped with tracers. In some examples, the multiphase fluid includes drilling muds, cement slurries, aerated muds, stable or unstable foams with variable rheologies.

Example conductivity probes disclosed herein may be deployed in different multiphase flow regime conditions, including varying gas volume fractions, water cuts, or water-in-liquid ratios. For purposes of this disclosure, it will be assumed that there are correlations between conductivity of water and its salinity. Such correlations may be determined from measurements, or inferred from empirical models or interpolation lookup tables, such as those disclosed in U.S. Pat. No. 6,831,470 or U.S. Pat. No. 9,528,869, both assigned to the present applicant.

In examples disclosed herein, flowback modeling can be performed based on a Mangrove™ and Kinetix™ software for multistage completion and stimulation design that is adapted to a well's specific geological, geochemical, and geo-mechanical conditions. The actual well flow can be continuously monitored using MPFM technology, such as Vx Spectra™ MPFMs available from Schlumberger, to accurately capture the rapid transient changes of produced fluids and sand content during FPDO and flowback operations, such as during the early flow in the life of the well. Real-time or substantially real-time transmission of the dynamic fluid and solids rate information to a coil tubing (CT) unit enables well operators to guide and manage injection, return rate, and pressure and to optimize inflow-outflow balance conditions. Accurate fluid and solid flow rate measurements provided by the MPFM in combination with a conductivity probe during FPDO and flowback operations, enables guided active control of CT injection parameters and the wellhead choke to keep wells in a defined, secure operating envelope to protect fracture connectivity and promote productivity.

In examples disclosed herein, the conductivity probe may be used during FPDO operations to simplify and enhance the quality of individual-phase flow-rate measurements with the MPFM (e.g., a Vx Spectra™ MPFM). Monitoring (e.g., at a high data-sampling frequency) pressure and flow rates in real-time or substantially real-time (e.g., during flow of the fluid through the MPFM) by using the MPFM may further identify changes in well performance. Another example use of the systems and methods disclosed herein is to monitor changes of salinity (i.e., water chemistry) of the produced water that are indicative of the progress of FPDO and flowback operations.

In order to monitor the flow rates of multiphase fluids more accurately and to substantially reduce or eliminate the need for post-processing of MPFM data acquired during FPDO and flowback operations, examples disclosed herein provide for automatic and continuous or substantially continuous tracking of brine salinity changes. In some disclosed examples, the MPFM monitors (e.g., at a high data-sampling frequency) pressure and flow rates in substantially real-time to further determine changes in well performance. In some disclosed examples, tracking changes in brine salinity change using a conductivity probe enables detection of the presence of sand slugs (e.g. to monitor well cleanup).

Figure 2:
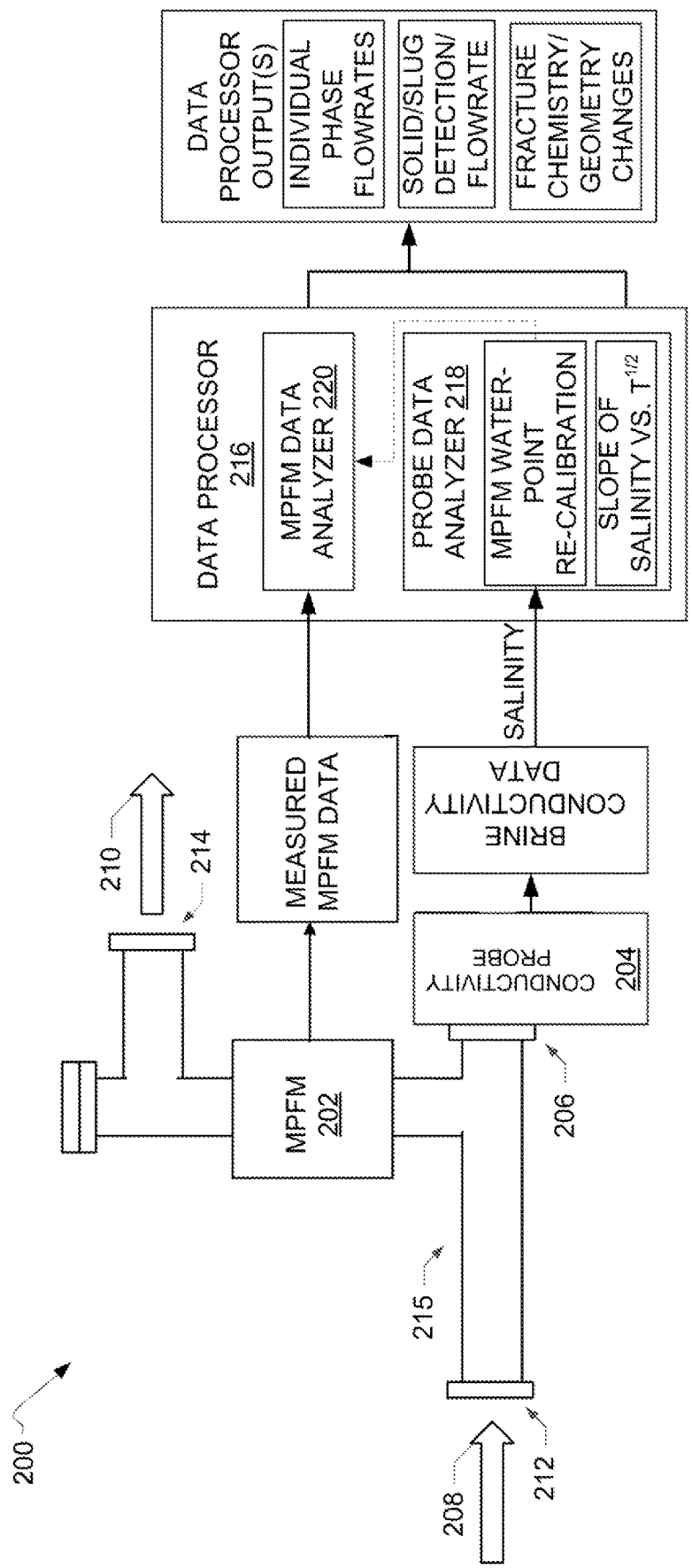
FIG. 2 is a schematic drawing of a first example conductivity probe system including a MPFM and a conductivity probe in accordance with teachings of this disclosure.

FIG. 2 illustrates a first example conductivity probe system 200 including a MPFM 202 (e.g., a Vx Spectra™ MPFM) and a conductivity probe 204 installed at a blind-tee inlet 206 (e.g., an end flange) of the MPFM 202. As disclosed herein, deployment of the MPFM 202 with the conductivity probe 204 enables improved measurement of the individual-phase holdup (e.g., fractional portions of each phase within a fluid traversed by gamma-ray or x-ray radiation beam) and flow rate of well fluids (e.g. gas, oil, and water) and/or solids during FPDO and flowback operations. In some examples, the MPFM 202 and the conductivity probe 204 may be used to detect the presence of solid (e.g., sand) slugs.

As represented by arrows 208, 210 in FIG. 2, fluid flowing between an inlet 212 and an outlet 214 of a fluid conduit 215 flows past the conductivity probe 204 and the MPFM 202. The example MPFM 202 generates fluid holdup data, flow rate data and/or other data for the fluid. The conductivity probe 204 generates brine conductivity data for the fluid. In the example of FIG. 2, the conductivity probe 204 measures the brine conductivity data in substantially real-time during fluid flow through the fluid conduit 215. In some examples, the conductivity probe 204 collects data substantially continuously during fluid flow. In other examples, the conductivity probe 204 collects data at predefined intervals of time (e.g., based on user settings). As discussed above, the brine conductivity data correlates to the salinity of the fluid (e.g., water). In the example of FIG. 2, the conductivity probe data is provided to a data processor 216.

The example data processor 216 of FIG. 2 is in communication with the MPFM 202 and the conductivity probe 204. The example conductivity probe system 200 of FIG. 2 can include data processors 216 in addition to those illustrated in FIG. 2. For instance, in some examples, the conductivity probe system 200 includes a data processor to receive and/or process data from the conductivity probe 204 before transmitting the conductivity probe data to the processor 216.

The example data processor 216 of FIG. 2 includes a probe data analyzer 218. The probe data analyzer 218 determines corrections, modifications, and/or calibrations for water to modify data measured by the MPFM 202, such as gamma-ray water attenuations. The probe data analyzer 218 transmits the data adjustments determined from the brine conductivity data collected by the conductivity probe 204 to a MPFM data analyzer 220 of the data processor 216. The MPFM data analyzer 220 uses data collected by the MPFM 202 and/or the conductivity probe 204 to generate fluid flow data outputs. The fluid flow data outputs can include, for example, one or more fluid holdups and flow rates for the respective phases of the fluid (e.g., oil flow rates, gas flow rates, water flow rates). In some examples, the MPFM data analyzer 220 of FIG. 2 detects the presence of solids and/or sand slugs and determines solid flow rates based on the data collected by the MPFM 202 and/or the conductivity probe 204. The outputs by the data processor 216 can include gas flow rate measurements, oil flow rate measurements, water flow rate measurements, identification of solids and/or sand slugs, and/or solid/sand flow rates.

In some examples, the probe data analyzer 218 determines a slope of changes in salinity versus time, which may be indicative of reservoir properties, such as changes in fracture chemistry/geometry and can be used to generate data outputs such as identification of fracturing stages. Thus, as compared to the known example of FIG. 1, the conductivity probe 204 of FIG. 2 provides for real-time monitoring of salinity conditions and eliminates or substantially eliminates the need for manual sampling and post-processing of MPFM data.

Figure 3:
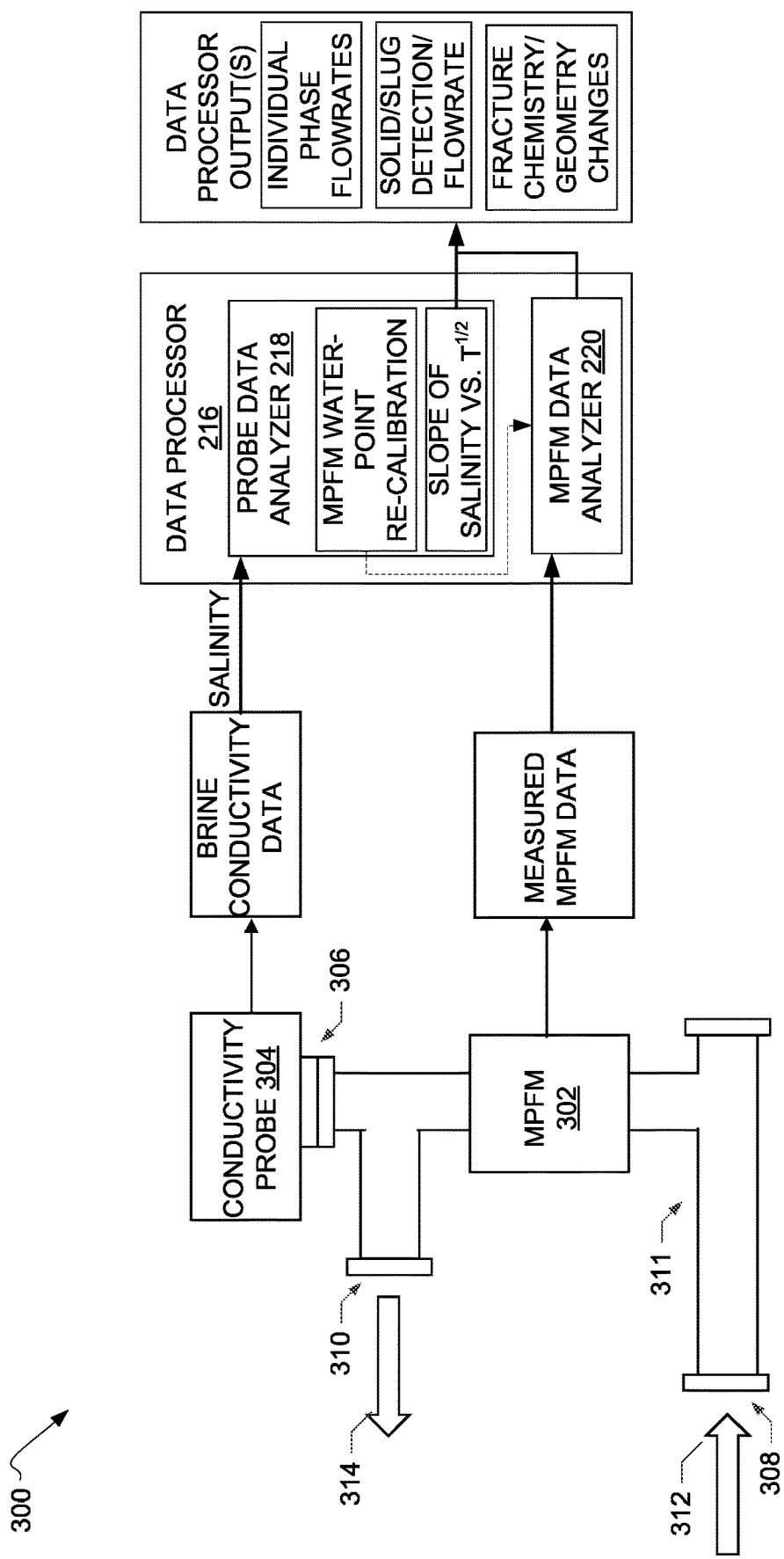
FIG. 3 is a schematic drawing of a second example conductivity probe system including a MPFM and a conductivity probe in accordance with teachings of this disclosure.

FIG. 3 illustrates a second example conductivity probe system 300 including a MPFM 302 (e.g., a Vx Spectra™ MPFM) and a conductivity probe 304. In the example of FIG. 3, the conductivity probe 304 is disposed at a vertical end-flange 306 of the MPFM 302. In the example of FIG. 3, the conductivity probe 304 is disposed at the vertical end-flange 306 to reduce opportunities for sand build-up on a measurement surface of the conductivity probe 304 as fluid flows past the conductivity probe 304 between an inlet 308 and an outlet 310 of a fluid conduit 311 (as represented by arrows 312, 314 of FIG. 3). The example conductivity probe system 300 of FIG. 3 includes one or more data processors, such as the data processor 216 of FIG. 2, to process the brine conductivity data measured by the conductivity probe 304 and/or fluid flow data measured by the MPFM 302 to generate one or more fluid flow data outputs. In the example of FIG. 3, the data processor 216 outputs, for instance, holdups and flow rates of the well fluids (e.g., gas, oil water) and solids and/or detects solid/sand slugs during FPDO and flowback operations, substantially as disclosed above in connection with FIG. 2.

Figure 4:
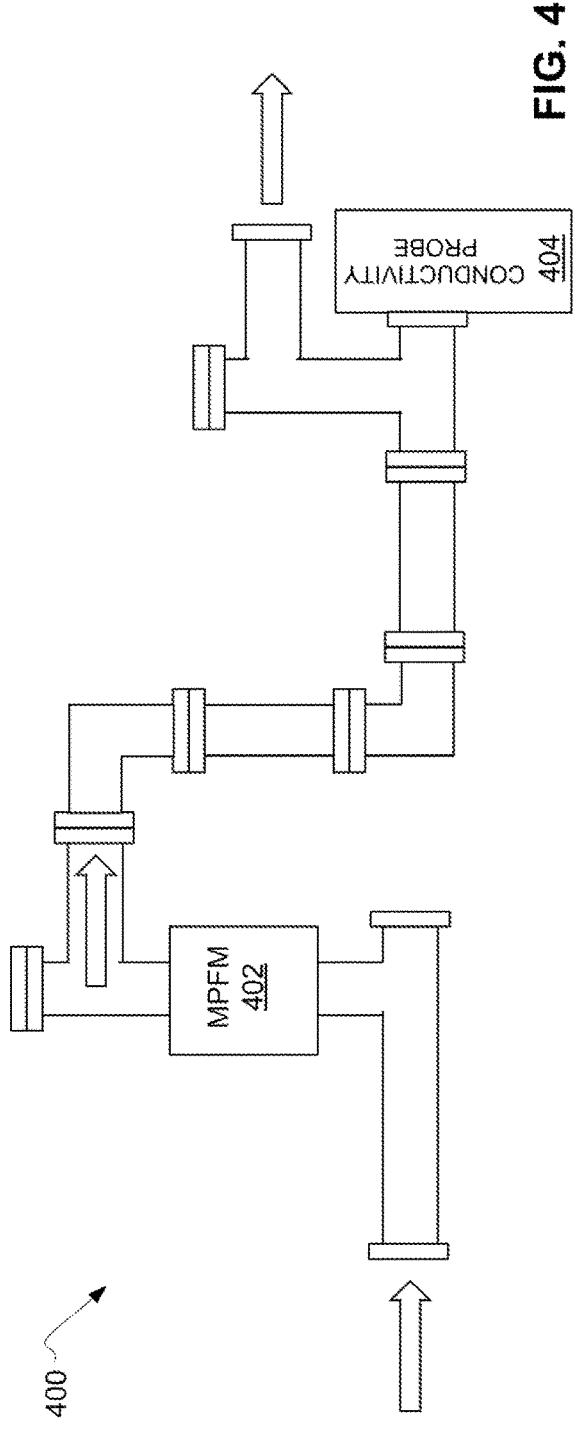
FIG. 4 is a schematic drawing of a third example conductivity probe system including a MPFM and a conductivity probe in accordance with teachings of this disclosure.
Figure 5:
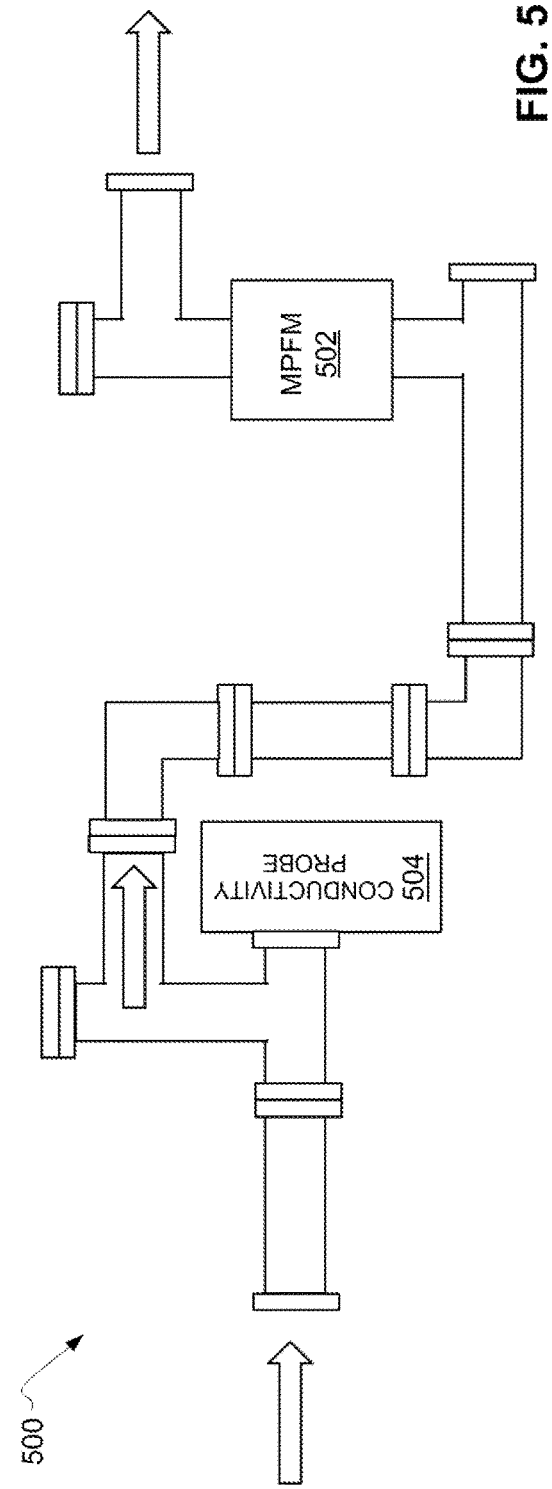
FIG. 5 is a schematic drawing of a fourth example conductivity probe system including a MPFM and a conductivity probe in accordance with teachings of this disclosure.

FIGS. 4 and 5 illustrate additional example conductivity probe systems including a MPFM and a conductivity probe in accordance with teachings of this disclosure. As shown in FIG. 4, a third example conductivity probe system 400 includes a MPFM 402 and a conductivity probe 404 disposed downstream of the MPFM 402. In some examples, the conductivity probe 404 is disposed downstream of a choke and/or downstream of a sand separator/catcher (or trap), where the choke and/or sand separator are located downstream of the MPFM 402 (i.e., between the MPFM 402 and the conductivity probe 404).

FIG. 5 illustrates a fourth example conductivity probe system 500 including a MPFM 502 and a conductivity probe 504 disposed upstream of the MPFM 502. The example systems 400, 500 of FIGS. 4 and 5 provide for substantially real-time monitoring of changes in water salinity. The conductivity probe data generated by the conductivity probes 404, 504 of FIGS. 4 and 5 can be provided to one or more data processors to enable improved measurements of the individual-phase holdups and flow rates of the well fluids (e.g., gas, oil, water), and/or to detect solids and/or sand slugs during FPDO and flowback operations, as discussed above in connection with FIGS. 2 and 3. In other examples, a conductivity probe may be coupled to a skid that is separate from an MPFM.

In some examples, computational corrections of flow rates measured by single phase flow meters or multiphase flow meters (e.g., the MPFM(s) 202, 302, 402, 502 of FIGS. 2-5) may be performed at the surface based on, for example, the data measured by the conductivity probe(s) 204, 304, 404, 504 of FIGS. 2-5. Thus, example data analyses disclosed herein may be performed by data processor(s) (e.g., the data processor 216 of FIGS. 2 and 3) disposed downhole, at the surface, or a combination thereof. In some examples, the flow rates measured based on the data collected using single phase or multiphase flow meter(s) and/or the conductivity probe(s) 204, 304, 404, 504 of FIGS. 2-5 may be used to control manual and/or automatic triggering of sampling operations.

While an example manner of implementing the example systems 200, 300, 400, 500 are illustrated in FIGS. 2-5, one or more of the elements, processes and/or devices illustrated in FIGS. 2-5 may be combined, divided, re-arranged, omitted, eliminated and/or implemented in any other way. Further, the example MPFM(s) 202, 302, 402, 502, the example conductivity probe(s) 204, 304, 404, 504, the example data processor 216, the example MPFM data analyzer 220, the example probe data analyzer 218 and/or, more generally, the example conductivity probe systems 200, 300, 400, 500 of FIGS. 2-5 may be implemented by hardware, software, firmware and/or any combination of hardware, software and/or firmware. Thus, for example, the example MPFM(s) 202, 302, 402, 502, the example conductivity probe(s) 204, 304, 404, 504, the example data processor 216, the example MPFM data analyzer 220, the example probe data analyzer 218 and/or, more generally, the example conductivity probe systems 200, 300, 400, 500 of FIGS. 2-5 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example MPFM(s) 202, 302, 402, 502, the example conductivity probe(s) 204, 304, 404, 504, the example data processor 216, the example MPFM data analyzer 220, the example probe data analyzer 218 and/or, more generally, the example conductivity probe systems 200, 300, 400, 500 of FIGS. 2-5 is/are hereby expressly defined to include a non-transitory computer readable storage device or storage disk such as a memory, a digital versatile disk (DVD), a compact disk (CD), a Blu-ray disk, etc. including the software and/or firmware. Further still, the example conductivity probe systems 200, 300, 400, 500 of FIGS. 2-5 may include one or more elements, processes and/or devices in addition to, or instead of, those illustrated in FIGS. 2-5 and/or may include more than one of any or all of the illustrated elements, processes and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

The expected changes of salinity that may be identified using the example conductivity probe(s) 204, 304, 404, 504 of FIGS. 2-5 are caused by four major phenomena: 1) Circulating water with coil tubing (CT) with a different salinity than the salinity of water that is present in the well and/or fracture system; 2) Production of water from leak-off that has leached some salts from the formation; 3) Production of reservoir water, whose salinity may be affected due to mixing with injected water from neighboring well(s) or zone(s); and 4) Injection of low salinity water in the annulus of the well to dissolve salt precipitation in tubing and circulated through a port in the completion. The first phenomenon is rapid and limited to FPDO. The second phenomenon is present during FPDO and flowback operations. The third phenomenon is generally limited to the latter part of the flowback or production period. The fourth phenomenon is consequent to remediation activities in high salinity formations to recover/protect flow productivity.

In some examples, samples of injected water may be collected at the coil tubing from a tank before being pumped in the well. The samples are used as an initial reference and the water of the samples is not the water that is present in the well that will be displaced by the injected water at the end of the coil. The sample fluid can be different from the displacement fluid used at the end of the hydraulic fracturing job (e.g., fluid in the wellbore at shut-in), leading to near instantaneous changes in salinity (higher or lower) once the FPDO begins. Furthermore, these changes to the fluid chemistry of the circulating fluid mixture can occur in a stepwise manner as each plug is drilled out due to the same phenomenon (e.g., changes in circulating fluid chemistry due to mixing with trapped plug to plug wellbore fluid).

When the hydraulic fracturing operations for each stage are completed, the completion fluid within that stage begins to interact with the formation and changes chemistry. Typically, this results in an increase in salinity, but the opposite has also been observed. This change in chemistry is time dependent (linear change in concentration vs $t^{1/2}$), as it is the result of the stimulation fluids mixing with the connate water within the stimulated zone (and in some cases, is also the result of dissolution of salts), as discussed herein. Because of this phenomenon it is expected that there will be subtle variations in the chemistry of each stage. These variations result in varying changes in salinity of the circulating fluid during FPDO as each subsequent stage is drilled out. The addition of a conductivity probe inline as in the example conductivity probe system 200 of FIG. 2 enables proper identification/calibration of these changes, and aids in the identification of stages that vary from design (e.g., different fracture chemistry or geometry).

The variation in produced water chemistry continues for a period of weeks to months depending on the salinity differences between the stimulation fluid and connate water and formation parameters (e.g. permeability, porosity, etc.). As a result of the highly reproducible square root of time dependence, most of the salinity changes occur early in the production period, which is when a MPFM is typically deployed. Continuous or substantially continuous monitoring of salinity changes via a conductivity probe as disclosed herein (e.g., the conductivity probe 204, 304, 404, 504 of FIGS. 2-5) provide for improved calibration of the MPFM (e.g., the MPFM(s) 202, 302, 402, 502 of FIGS. 2-5) with respect to gamma-ray water attenuation via the identification/characterization of this phenomenon in each well.

As production continues into the latter part of the production period, the aforementioned changes in the water chemistry can deviate due to changes in the fracture geometry. In known systems (e.g., the known system 100 of FIG. 1), this phenomenon is typically identified via manual water sampling and analysis. However, a conductivity probe (e.g., the conductivity probe(s) 204, 304, 404, 504 of FIGS. 2-5) can be used to identify changes in water chemistry based on continuous or substantially continuous monitoring of the produced water conductivity/salinity (e.g., measured inline under multiphase flow conditions). In some examples, periodic water-sample chemistry analyses may be collected for validation or generation of a conductivity-to-salinity model, or an ion-selective electrode may be installed to monitor the changes in an individual ion concentration over time. The detection of salinity changes enables an update of brine density that is used in the computation of bottom-hole pressure in the workflow.

The example conductivity probe(s) 204, 304, 404, 504 of FIGS. 2-5 may be used in other types of applications, such as circulation applications, injection applications, flowing applications, pipeline applications, coil tubing milling applications, correction/computation of flow rate applications, and determination of ion composition. In circulation applications, a circulation of fluids is established between an injection point and a return point and the conductivity probe (or a combination of such probes) monitors the flow in various places or flow regimes. A well can include an underground pipe with several drains or ramifications connected to each other. There may be several drains connected to the well. Example circulation applications include, for instance, drilling, coil tubing drilling, coil tubing milling, coil tubing monitoring, acidizing with return, fracturing with return, coil tubing or tubing cleaning of wells, direct circulation to displace fluids in a well, reverse circulation to displace fluids in a well, steam cycling, annular leak detection, and inter-well or inter-drain, or intra well interference monitoring and testing (during production, injection or stimulation).

Another example application in which the example conductivity probe(s) 204, 304, 404, 504 of FIGS. 2-5 may be used includes injection applications, such as water conformance, water injection, gas injection, oil/gas storage, water storage, steam injection, steam quality monitoring, and huff and puff (huff portion). Huff and puff refers to a cyclic process in which a well is injected with a recovery enhancement fluid and, after a soak period, the well is put back on production. Flowing applications may include, for instance, water monitoring (including first water), tracer monitoring, huff and puff (puff portion). Pipeline applications may include, for instance, fluid displacement in pipeline and pig marking/monitoring.

In coil tubing milling applications, water is used as a drilling and/or power fluid with or without additives to drill through plugs in multistage frac wells. The geological formations may contribute some fluids of various compositions including water that can be of a varying salinity. The variations in salinity may be because the water is naturally doped with some salts or because of an artificial intervention that has changed the initial salinity of the in situ water. The variations in salinity may be because the presence of the water is the result of a prior operation involving injection of water with a different salinity, where the salinity may have changed as a function of time during injection or while the water was present in the formation, the induced fractures, or the wellbore. The injection of water may have been in the same well and/or drain or from a different drain or combination thereof, or a different well. By collecting measurements of the injected water conductivity and of the produced water conductivity via the example conductivity probe(s) 204, 304, 404, 504 of FIGS. 2-5, the following example parameters can be inferred: relative ratio of injected water versus produced water, position of the produced water entries, dynamics of the leaching of the water in contact with the formation, and efficiency of the water displacement.

Another example application in which the example conductivity probe(s) 204, 304, 404, 504 of FIGS. 2-5 may be used includes determining ion composition from conductivity data. For example, when combined with periodic sampling and chemical analysis of the produced water, the conductivity of the fluid can be used to infer compositional changes over time in the water during the aforementioned applications.

Flowback Analysis of Illustrative Wells

As treatment fluid interacts with freshly cleaved rock surfaces during the process of hydraulic fracturing, the equilibrium condition within the rock is disrupted. A combination of factors such as high pressure, favorable wettability, clay reactivity, and high osmotic potentials can lead to substantial imbibition of fracturing fluid into the reservoir. The imbibition of this relatively fresh water results in a disruption to the local chemical equilibrium. As the connate water becomes diluted, some solid state minerals dissolve and enrich the connate water with the associated ions, such as $Ca^{+2}$ and $CO3^{-2}$ ions. In a simultaneous process, the dilution of the connate water also results in a change in the absorbed cations on clay surfaces. This is due to a process known as the valence dilution effect, which is an effect driven by the preference for multivalent cations over monovalent cations for charge balance at the clay surface. In cases where the fracturing fluid is laden with salt, either due to water re-use or clay reactivity considerations, the clay-connate water equilibrium can be further disrupted.

Finally, the dilution of the connate water is counteracted by the vast quantities of salt found within the nearby rock. This results in a gradual increase in the overall salt concentration in the near fracture region. This effect is manifested in the gradual increase in flowback water salinity over time, typically exhibiting a linear increase with the square root of time (i.e. diffusion limited).

Figure 6:
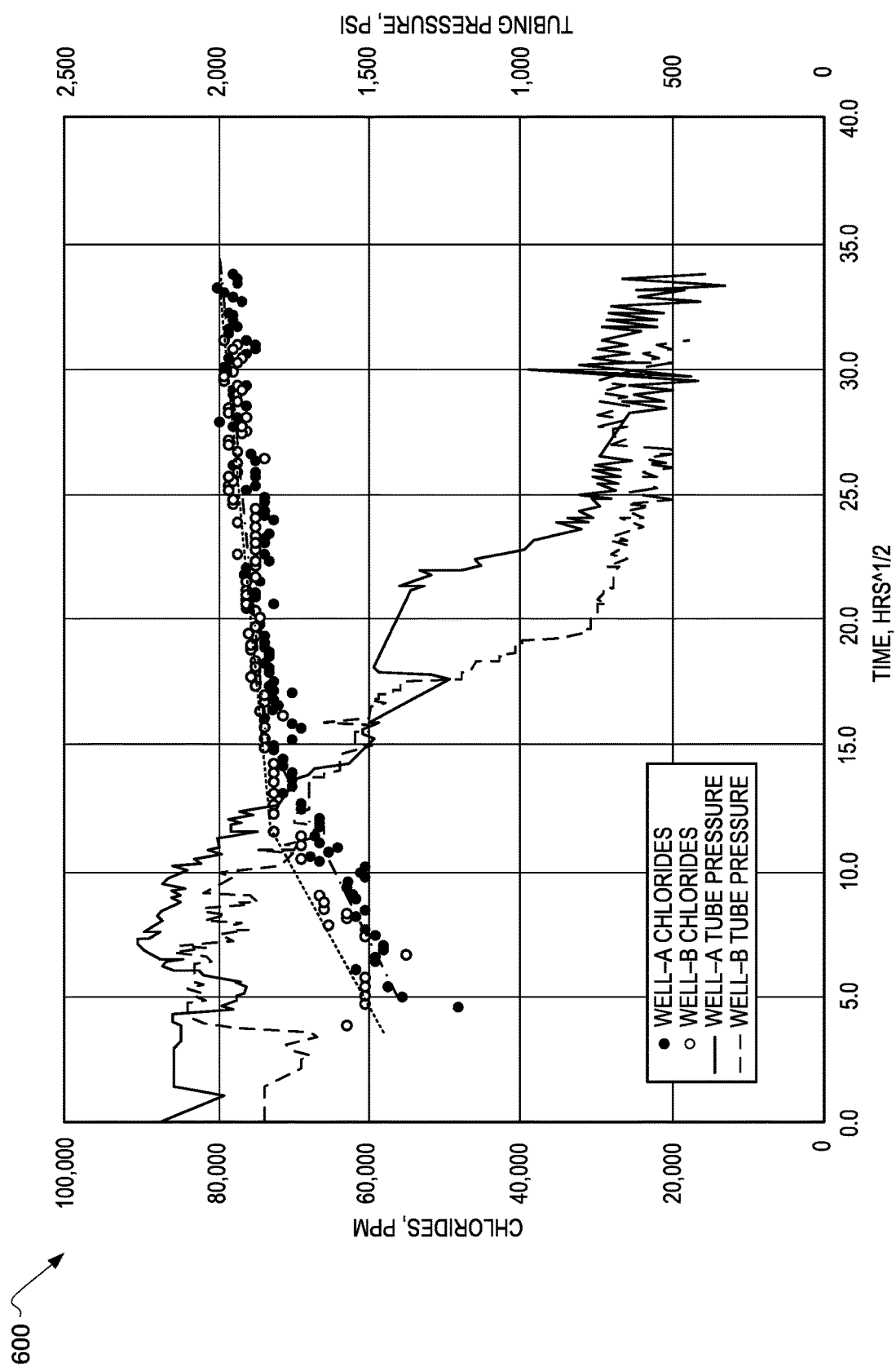
FIG. 6 is a graph of chloride concentration and tubing pressure as a function of time for flowback analysis according to teachings of the disclosure.

FIG. 6 is an example graph 600 of chloride concentration and tubing pressure as a function of time. Field measurements of chloride concentrations for a first well, Well-A, and a second well, Well-B, show a change in slope midway through the flowback period. This may indicate a change in the connected fracture geometry. As shown in FIG. 6, both the first and second wells exhibited a change in chemical behavior at a tubing pressure of approximately 1,700 psi (5,400 psi bottom hole pressure).

As shown in the graph 600 of FIG. 6, the first well, Well-A, and the second well, Well-B, exhibited a linear trend in slope change (where Chloride Cl— is a proxy for salinity), although the slope changed midway through the flowback period. This change, when considered along with additional chemical data, indicates a change in the conductive fracture geometry during the flowback period of both wells.

In operation, the slope change in the chloride concentrations observed in FIG. 6 may correspond to chemistry changes observed in the flowback water (not shown in FIG. 6). The large number of ions exhibiting this change in chemistry at the transition point may be a result of a change in the fracture geometry. As discussed herein, flowback water chemistry changes constantly over time as the fluid in the fracture network and the formation chemistry equilibrate. This process can take several months in some reservoirs, and is typified by a constant slope defined by the fracture geometry and reservoir contact. In the case of the first well Well-A of FIG. 6 (and the second well Well-B according to the field chlorides measurements), this was only the case for a short period of time, after which a different slope emerged from the data. Furthermore, this change in chemical behavior coincides with a tubing pressure of 1,700 psi, or 5,400 psi bottom hole pressure (FIG. 6) and a change in the production performance of the wells (not shown). Such changes point to a mechanism of either a change in the fracture geometry (i.e., closure of a previously contributing fracture geometry) or contribution of produced fluids from a somewhat under-pressured zone.

MPFM Field Operations With Usage of a Conductivity Probe

An example field operation involving a MPFM (e.g., the MPFM(s) 202, 302, 402, 502 of FIGS. 2-5) involves rig-up/installation (e.g., by an operator) and fluids calibration for the MPFM. A conductivity probe (e.g., the conductivity probe(s) 204, 304, 404, 504 of FIGS. 2-5) may be disposed at an end-flange of a blind-tee inlet of the MPFM (e.g., as in the example of FIG. 2), at a vertical blind-tee end flange (e.g., as in the example of FIG. 3), or downstream of a choke if there are issues related to the pressure or sand (e.g., as discussed in connection with FIG. 4).

A sample of injected water can be collected (e.g., prior to the operation). A data processor (e.g., the data processor 216 of FIGS. 2 and 3) associated with the conductivity probe(s) 204, 304, 404, 504 may use a default lookup table of the relationship between NaCl brine conductivity/salinity and gamma-ray mass attenuation. As disclosed in U.S. Pat. Nos. 6,831,470 and 9,528,869, waters of salt species from a prior well or prior water mixes may be performed with in-situ verification at the base prior to the operation.

In the example field operation, a pressure test is performed with CT (coil tubing) water. The CT is run in hole. Even if no fluid is pumped, there will be return of water in the flowline due to the injection of, for instance, the steel CT in the well. During circulation, a slug of heavy hydrocarbon (e.g., having density close to 1000 kg/m$^3$) may be observed. The oil slug may last few minutes and can include 100% (or substantially 100%) grease (e.g., the slug may be a lubricant related to the CT or completion operations that is displaced out of the well). The period in which the slug is substantially entirely grease is usually followed by 100% (or substantially 100%) water for 30 minutes or more.

In the example field operation, the variations of the brine conductivity can trigger collection of samples of water (e.g., manual or automated sampling using a sampler). Such samples provide indications of statuses of the circulation and displacement of the fluids inside the wellbore. The triggering mechanism may be based on a particular (e.g., predefined) threshold level of uncertainty that is deemed acceptable for the computation of the water, oil, gas, and solid rates.

In the example operation, the net fluid volume produced by the formation/fracture is provided in real-time to the CT control unit. The net fluid volume can be calculated from the difference of the total produced fluid measured by the MPFM at surface and corrected to the current brine salinity as tracked by the conductivity probe(s) 204, 304, 404, 504, and to the bottom-hole pressure and temperature conditions and the injected volumes in the CT. In some examples, an operator keeps the FPDO at balance at bottom-hole conditions (no inflow, no outflow) or under a controlled imbalance condition (pre-defined or optimized on the fly).

In the example field operation, the substantially real-time tracking of the brine salinity changes by the conductivity probe(s) 204, 304, 404, 504 of FIGS. 2-5 may be used to detect sand with the MPFM. For instance, if there are or were conditions of inflow (which usually occur as choke control at surface may be challenging), an operator can observe a slug of sand transported up to the surface after travelling from bottom of the well. The operator may correlate these events with the instantaneous underbalance monitored flow rate. There may be conditions where the well was underbalance (inflow condition) but would still remain in the secure part of a secure operating envelope (SOE), or a combination of operational parameters that preserve the connection between fractures and the wellbore. In such examples, no sand or substantially no sand would be observable at the surface. In examples in which the operation moves into a first zone of the SOE, short sand bursts may be observed. If the example operation moves into a second zone of the SOE, longer sand events with larger quantities may be observed. If sand is observed when the operator expects to be in a third zone of the SOE, then the model may need to be recalibrated and re-adjusted to secure the operating envelope.

In the example operation, sand production may be substantially accurately quantified based on sand mass rate. Sand events may last from, for instance, 30 seconds to 10 minutes. Fracking jobs, however, should not be operated in conditions of continuous sand production. An example threshold of sand detection may be 0.5% in mass. In some examples, the threshold may be to detect 1-kg of sand production in a minute. For example, it has been observed during testing with a conductivity probe that the salinity measurement was largely unaffected with the presence of suspended sand in water. Thus, certain quantities of sand produced would not significantly impact the computation of volumes of fluids produced. In some examples, it may be valuable to estimate water cut and/or gas/oil ratio (GOR) if sand and/or or change of salinity are observed.

In the example operation, water density measurements may be monitored to provide a more accurate computation of bottom hole pressure conditions using a pipe pressure simulation model. A change of salinity may also be the expression of a change of density. Upon detection of the salinity change (e.g., based on data obtained from the conductivity probe(s) 204, 304, 404, 504), a look-up table can be used to correct, for example, the density of the water phase for calculations of bottom-hole pressure.

In the example operation, the aforementioned field information may be streamed in real-time or substantially real-time to associated software components (e.g., implemented by one or more data processors such as the data processor 216 of FIGS. 2 and 3). In some examples, the field information is stored in one or more cloud-based locations and/or collated into a single report.

Correction of MPFM Gamma-Ray Measurement by Conductivity Probe

As represented in FIGS. 2 and 3, the data processor(s) 216 determine one or more characteristics of the multiphase fluid based on data measured by a MPFM (e.g., the MPFM(s) 202, 302, 402, 502 of FIGS. 2-5), such as individual phase holdups and flow rates of oil, gas, water and solids/sand. Gamma-ray attenuation coefficients can be calculated from measured count-rates, pressure and temperature data collected by the MPFM. The attenuation coefficients can be stored in a memory of the data processor(s) 216. Also, as disclosed herein, the attenuation coefficients can be adjusted by the data processor(s) 216 based on brine conductivity and/or salinity measurements from a conductivity probe (e.g., the conductivity probe(s) 204, 304, 404, 504 of FIGS. 2-5) by using one or more correlations between attenuation coefficients and other parameters (e.g. temperature and parameters representative of complex permittivities derived from measurements of the conductivity probe system, as disclosed herein).

The example MPFM(s) 202, 302, 402, 502 of FIGS. 2-5 can include an emitter and detector of electromagnetic radiation, which enable measurement of attenuation data for fluid flowing along a portion of the fluid conduit 215, 311 of the MPFM(s) 202, 302, 402, 502 (e.g., a measurement section of the fluid conduit). Some of the electromagnetic radiation is absorbed by the fluid, but a portion of the electromagnetic radiation is received by the detector. The emitter can produce electromagnetic radiation of any suitable frequency and energy within the electromagnetic spectrum. For instance, in some examples the emitter includes one or more radioactive sources that emit gamma rays and X-rays. Other examples could include non-radioactive emitters, such as electric X-ray generators.

The emitter and the detector of the example MPFM(s) 202, 302, 402, 502 of FIGS. 2-5 can be positioned on opposite sides of a fluid conduit, such as a portion (e.g., a measurement section) of the fluid conduit 215, 311 of FIGS. 2 and 3. A linear attenuation coefficient, $\lambda_m(E)$, of the fluid for gamma-ray or x-ray electromagnetic radiation at a given energy E can be measured according to the Beer-Lambert law:

$$\lambda_m(E) = \frac{1}{d}\ln(N_0(E)/N(E)) \quad (1)$$

in which d is the diameter of the portion of the fluid conduit 215, 311 through which the radiation is directed, N(E) is the amount of transmitted photons (the count rates or the quantity of photons detected by the detector), and $N_o(E)$ is the empty pipe count rates (the quantity of photons emitted from the emitter that would have reached the detector with no fluid in the measurement section of the fluid conduit 215, 311).

The analyzed fluid can have multiple phases. For example, the fluid can be a multiphase fluid having an oil phase, a water liquid phase, a gas phase, and solids (sand) phase. The attenuation of gamma-ray or x-ray electromagnetic radiation by a multiphase fluid is a linear combination of the attenuations caused by each of its phases weighted by their proportions in the fluid. In the case of a fluid having some combination of gas, oil, water and solids, this can be written as:

$$\lambda_m(E)=\lambda_g(E)\alpha_g+\lambda_o(E)\alpha_o+\lambda_w(E)\alpha_w+\lambda_s(E)\alpha_s \quad (2)$$

where $\lambda_g(E)$, $\lambda_o(E)$, $\lambda_w(E)$ and $\lambda_s(E)$ are attenuation coefficients for gas, oil, water, and solids for radiation of a given energy level E, and $\alpha_g$, $\alpha_o$, $\alpha_w$ and $\alpha_s$ are respective fractional portions of each phase within the analyzed fluid traversed by gamma-ray or x-ray radiation beam (also referred to as phase holdups or phase fractions). This gives as many equations as the number of distinct energy levels in the electromagnetic radiation from the emitter of the example MPFM(s) 202, 302, 402, 502 (further considering that the all phase holdups sum up to unity). For a system including a MPFM (e.g., the example conductivity probe systems 200, 300, 400, 500 of FIGS. 2-5) with an appropriately chosen radioactive source (such as $^{133}$Barium) exhibiting at least three distinct energy levels, the following system of linear equations can be obtained:

$$\begin{bmatrix} \lambda_g(E_1) & \lambda_o(E_1) & \lambda_w(E_1) & \lambda_s(E_1) \\ \lambda_g(E_2) & \lambda_o(E_2) & \lambda_w(E_2) & \lambda_s(E_2) \\ \lambda_g(E_3) & \lambda_o(E_3) & \lambda_w(E_3) & \lambda_s(E_3) \\ 1 & 1 & 1 & 1 \end{bmatrix} \begin{bmatrix} \alpha_g \\ \alpha_o \\ \alpha_w \\ \alpha_s \end{bmatrix} = \begin{bmatrix} \lambda_m(E_1) \\ \lambda_m(E_2) \\ \lambda_m(E_3) \\ 1 \end{bmatrix} \quad (3)$$

The 4×4 attenuation matrix A above (i.e. the matrix including the phase-specific attenuation coefficients for three appropriately chosen energy levels) can be obtained from full-pipe measurements on each phase, hereafter called the in-situ references, or theoretical coefficients can be used. This attenuation matrix may then be mathematically inverted directly or indirectly (giving an apparent inversion matrix A-1) to calculate the phase holdups:

$$\begin{bmatrix} \alpha_g \\ \alpha_o \\ \alpha_w \\ \alpha_s \end{bmatrix} = \begin{bmatrix} \lambda_g(E_1) & \lambda_o(E_1) & \lambda_w(E_1) & \lambda_s(E_1) \\ \lambda_g(E_2) & \lambda_o(E_2) & \lambda_w(E_2) & \lambda_s(E_2) \\ \lambda_g(E_3) & \lambda_o(E_3) & \lambda_w(E_3) & \lambda_s(E_3) \\ 1 & 1 & 1 & 1 \end{bmatrix}^{-1} \begin{bmatrix} \lambda_m(E_1) \\ \lambda_m(E_2) \\ \lambda_m(E_3) \\ 1 \end{bmatrix} = A^{-1} \begin{bmatrix} \lambda_m(E_1) \\ \lambda_m(E_2) \\ \lambda_m(E_3) \\ 1 \end{bmatrix} \quad (4)$$

Note that matrix A contains linear attenuation coefficients of all the individual phases $\lambda_i(E_j)$ (i='o', 'g', 'w', 's'; j=1, 2, 3). If there are changes in the fluids properties from the values of the in-situ references, such as a change in the water salinity sal (in weight percentage), this will cause a change in the brine mass attenuation coefficient $\mu_w(E_j)$ as follows (where $\mu_{H2O}$ and $\mu_{salt-species}$ are mass attenuation coefficients of pure water and the salt species in water, such as sodium chloride NaCl), $$\mu_w(E_j)=(1\text{sal})\times\mu_{H2O}(E_j)+\text{sal}\times\mu_{salt-species}(E_j) \quad (5a)$$

$$\Delta\mu_w(E_j)=(\mu_{salt-species}(E_j)\mu_{H2O}(E_j))\Delta\text{sal} \quad (5b)$$

and, thus, there will be a change in the brine linear attenuation coefficient $\lambda_w$ ($E_j$):

$$\lambda_w(E_j) = \rho_w(sal; p, T) \times \mu_w(E_j) \quad (6a)$$

$$\Delta\lambda_w(E_j) = \rho_w(sal; p, T) \times \Delta\mu_w(E_j) + \Delta\rho_w(sal; p, T) \times \mu_w(E_j) \quad (6b)$$

where pw(sal; p, T) is the density of the brine water, which is also pressure p and temperature dependent. The detection of salinity change may enable an update of brine density that is used in the computation of MPFM mixture density and individual flow rates (e.g., by the data processor(s) 216), and of the bottom hole pressure in the workflow for modeling of the fractured well.

As implied by equation (4), there will be errors in the calculations of the individual phase holdups $\alpha_i$(i='o', 'g', 'w', 's') if there is no update in the brine linear attenuation coefficient $\lambda_w(E_j)$. This may result in errors in the individual phase volumetric (or mass) flow rates which are directly proportional to the respective individual phase holdups.

The example conductivity probe(s) 204, 304, 404, 504 of FIGS. 2-5 can provide online (e.g., substantially real-time and/or substantially continuous) measurement of brine conductivity under multiphase flow conditions, and, thus, online tracking of changes in brine salinity sal, making corrections in brine mass attenuation coefficient $\mu_w(E_j)$ and brine linear attenuation coefficient $\lambda_w(E_j)$, according to equations (5) to (6).

In some examples, the conductivity probes of FIGS. 2-5 may be realized by an RF/microwave transmission sensor, a reflection sensor, and/or a resonance sensor. In such examples, the determination of brine conductivity and/or salinity may be based on a method of interpreting the measured multiphase-flow mixture complex permittivity ($\epsilon^* = \epsilon' - j\epsilon''$), such as those disclosed in U.S. Pat. No. 6,831, 470. The use of a radio-frequency (RF)/microwave open-coaxial reflection probe in connection with such a method is discussed in connection with FIGS. 7-9.

In the conductivity probe systems 200, 300, 400, 500 of FIGS. 2 to 5, a brine-water dielectric-model can be used to determine (e.g., by interpolation) directly multiphase flow brine-water salinity (s) and/or brine-water dc-conductivity ($\sigma_{dc}$), and the brine density $\rho_w$ and mass attenuation coefficient $\mu(E)$, given the measured water-rich flow-mixture complex-permittivity ratio ($\epsilon''/\epsilon'$) and the measured flow temperature T and pressure p.

Figure 7:
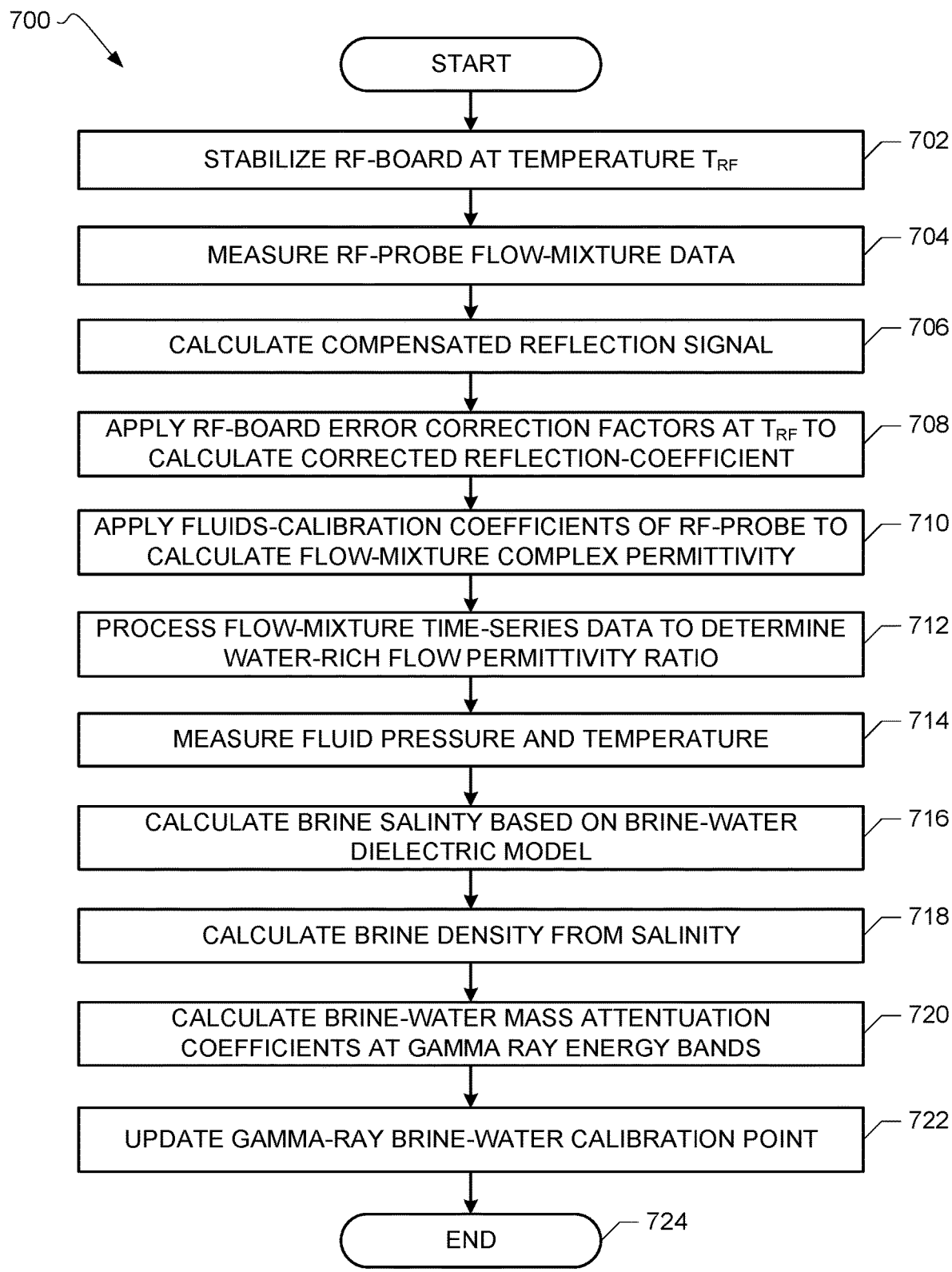
FIG. 7 is a flowchart of an example method that may be executed to process data measured via the example conductivity probe systems of FIGS. 2-5.
Figure 8:
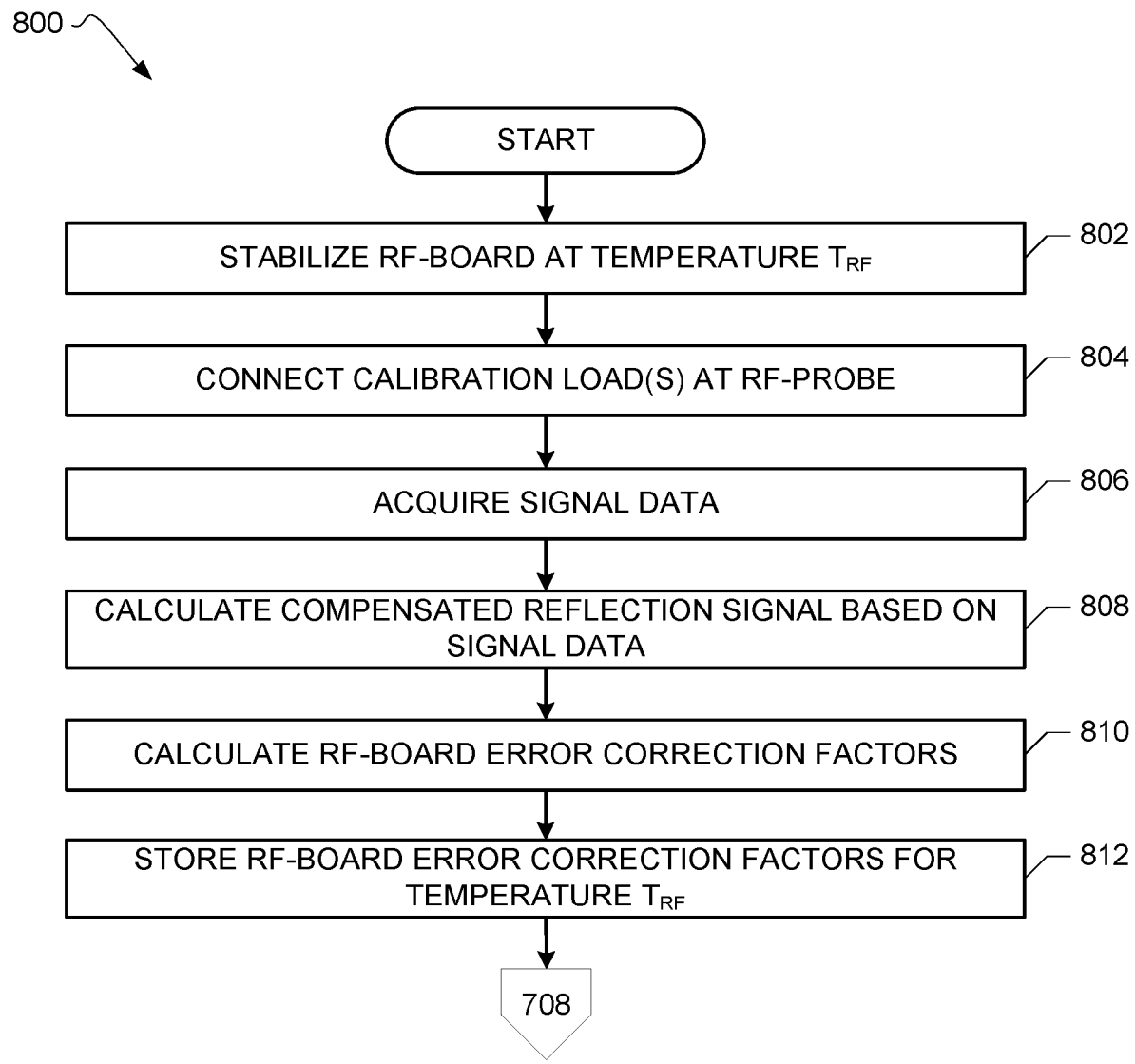
FIG. 8 is a flowchart of an example method that may be executed to process data measured via the example conductivity probe systems of FIGS. 2-5.
Figure 9:
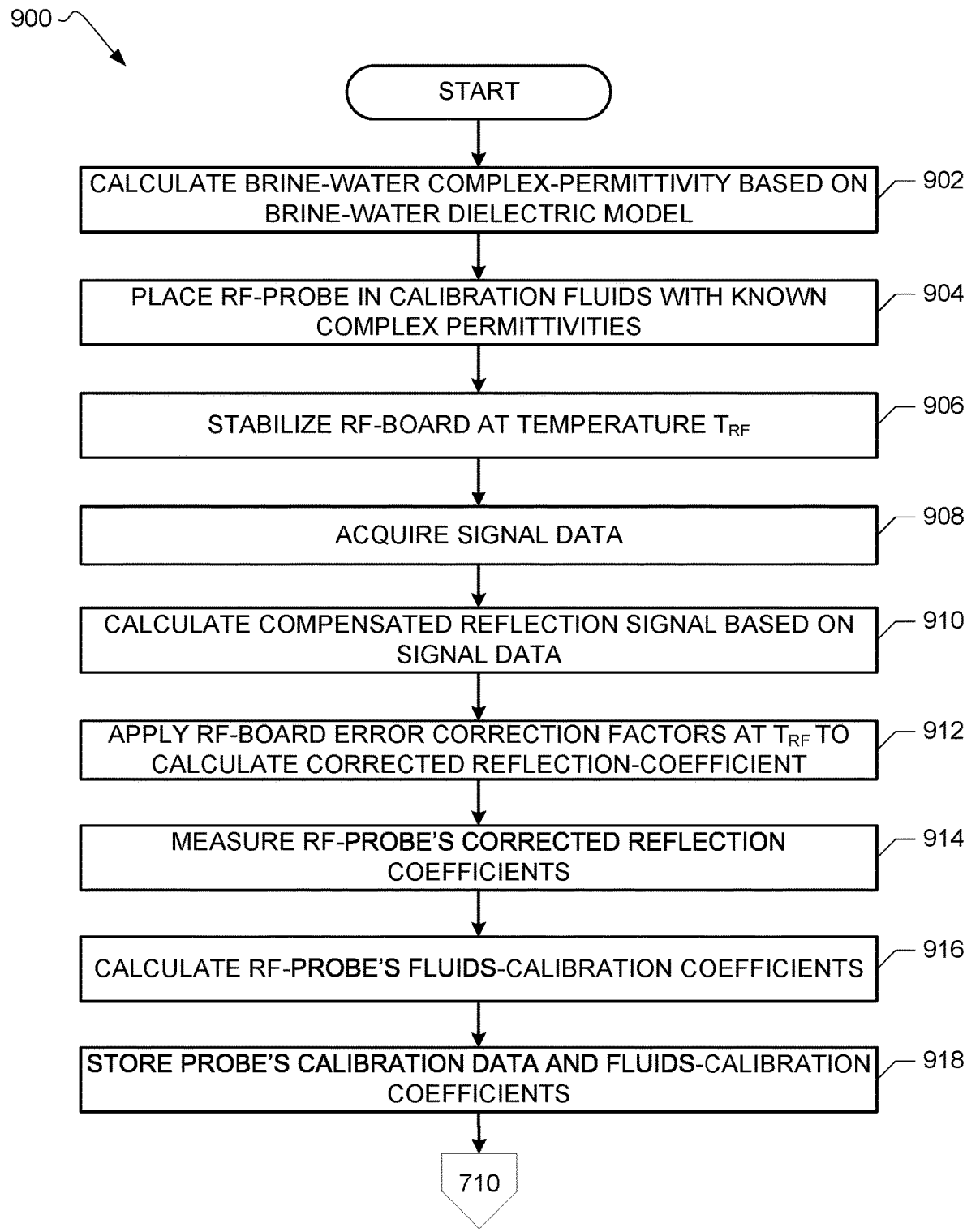
FIG. 9 is a flowchart of an example method that may be executed to process data measured via the example conductivity probe systems of FIGS. 2-5

The example methods of FIGS. 7-9 include calibrating the probe using at least three reference fluids, such as dry-air, fresh water, and brine-water of an appropriate salinity (and may be a metallic short-circuit to cover high effective water-conductivity conditions). The reference values of the complex permittivity of those waters (needed for the probe calibration) can be provided by a brine-water dielectric-model (functions of water salinity, salt species such as NaCl, temperature, pressure and RF/microwave frequency), given the dc-conductivity and temperature of those calibration waters (measured by a laboratory conductivity sensor).

In the example methods of FIG. 7-9, the same brine-water dielectric-model can be mapped (for several pressures, salt species) for establishing the correlations of the brine-water complex-permittivity ratio ($\epsilon''/\epsilon'$) as a function of salinity and temperature, for one or more chosen RF/microwave frequency. In the example methods of FIGS. 7-9, the established correlations are used to determine by interpolation brine-water salinity of a multiphase flow, given the water-rich multiphase flow-mixture complex-permittivity ratio ($\epsilon''/\epsilon'$)$_{mixture}$ measured by the RF/microwave probe, and the flow temperature measured by a temperature probe.

The self-consistency of the brine-water dielectric-model, used for both calibrating the probe and interpreting the probe-measured complex-permittivity ratio, yields a robust water-salinity (and conductivity) estimate. Potential in-situ calibration and/or validation of the MPFM (e.g., the MPFM(s) 202, 302, 402, 502 of FIGS. 2-5) and/or conductivity probe (e.g., the conductivity probe(s) 204, 304, 404, 504 of FIGS. 2-5) by using the data of the detected fresh water slugs may be performed.

FIG. 7 is a flowchart of an example method 700 for determining brine conductivity and/or salinity. The example method 700 can be implemented by analyzing multiphase-flow mixture complex permittivity measured using a conductivity probe (e.g., the conductivity probe(s) 204, 304, 404, 504 of FIGS. 2-5). As discussed above, in the example method 700 of FIG. 7, the conductivity probe may be a radio-frequency (RF)/microwave open-coaxial reflection probe. The example method 700 of FIG. 7 may be implemented by one or more data processors (e.g., the data processor(s) 216 of FIGS. 2 and 3) located at the surface, downhole, or a combination thereof.

Referring to FIG. 7, the example method 700 includes stabilizing an RF-board (including one or more measurement electronics) associated with the RF-probe at a set of pre-characterized/pre-calibrated temperatures TRF, relative to an ambient temperature range (block 702).

The example method 700 of FIG. 7 includes measuring RF-probe flow mixture data at a frequency f (block 704). Measuring the RF-probe flow mixture data can include, for instance, acquiring a reflection path signal $V_{RC}$ and an incident path signal $V_{MC}$ via the RF-probe. The example method 700 includes calculating a compensated reflection signal p (block 706). The compensated reflection signal p can be calculated as:

$$\rho = \frac{V_{RC}}{V_{MW}} \quad (7)$$

The example method 700 of FIG. 7 includes applying RF-board correction factors ($E_d$, $E_s$, $E_f$) for the stabilization temperature $T_{RF}$ to calculate a corrected reflection-coefficient $\Gamma$ (block 708). The RF-board correction factors ($E_d$, $E_s$, $E_f$) can be considered a first set of correction factors that are obtained during the RF-board electronics factory calibration and stored in a memory in communication with the data processor(s) 216 of FIGS. 2 and/or 3 (as discussed in connection with FIG. 8). The corrected reflection-coefficient $\Gamma$ can be calculated as:

$$\Gamma = \frac{\rho - E_d}{E_s(\rho - E_d) + E_f} \quad (8)$$

The example method 700 of FIG. 7 includes applying fluids-calibration coefficients (A, B) of the RF-probe to calculate flow-mixture complex permittivity $\epsilon^*$ (block 710). The fluid-calibration coefficients (A, B) can be considered a second set of correction factors that are obtained during factory calibration or at a wellsite and stored in a memory in communication with the data processor(s) 216 of FIGS. 2 and/or 3 (as discussed in connection with FIG. 9). The flow-mixture complex permittivity $\epsilon^*$ can be calculated as:

$$G = \frac{\Gamma_{ref} - \Gamma}{\Gamma_{ref} + \Gamma} \quad (9)$$

-continued $$\varepsilon = \frac{AG + \varepsilon_{ref}}{1 - BG} \quad (10)$$

The example method 700 of FIG. 7 includes processing flow-mixture complex permittivity ε* time-series data to determine a water-rich flow permittivity ratio $$\left(\frac{\varepsilon''}{\varepsilon'}\right)$$

(block 712).

The example method 700 of FIG. 7 includes measuring fluid temperature T and pressure p (e.g., via temperature and pressure sensors) (block 714). The example method 700 of FIG. 7 includes calculating brine salinity s using a brine-water dielectric model as function of temperature, pressure, and salt species (block 716). The brine-water dielectric model may be stored in a memory in communication with the data processor(s) 216 of FIGS. 2 and/or 3. The brine salinity s can be calculated as follows:

$$(s; \sigma_{dc}) = func\left(\left(\frac{\varepsilon''}{\varepsilon'}\right), T; p\right)_{f;salt-species} \quad (11)$$

In some examples, dc-conductivity $\sigma_{dc}$ may also be calculated.

The example method 700 of FIG. 7 includes calculating brine density $\rho_w$ from the salinity s (block 718). The brine density $\rho_w$ can be calculated using fluid pressure p and temperature T as inputs. The example method 700 includes calculating brine-water mass attenuation coefficients μ(E) at gamma-ray energy bands (E) using, for example, equation (5a), above (block 720). The example method 700 of FIG. 7 ends with updating gamma-ray brine-water calibration point (block 722).

FIG. 8 is a flowchart of an example method 800 to determine the conductivity probe RF-board error-correction factors ($E_d$, $E_s$, $E_f$) (i.e., the first set of correction factors) discussed in connection with FIG. 7, at one or more RF-board thermal-stabilization temperatures $T_{RF}$. The example method 800 of FIG. 8 may be implemented by one or more data processors (e.g., the data processor(s) 216 of FIGS. 2 and 3) located at the surface, downhole, or a combination thereof.

The example method 800 of FIG. 8 includes stabilizing the RF-board (including one or more measurement electronics) at a temperature $T_{RF}$ (block 802). The example method 800 of FIG. 8 includes connecting, in turn, respective calibration loads at the RF-probe (block 804). The calibration loads include an open circuit ("oc") associated with a reference value $\Gamma_{oc}$, a short circuit ("sc") associated with a reference value $\Gamma_{sc}$, and a matched load ("zo") associated with a reference value $\Gamma_{zo}$.

The example method 800 of FIG. 8 includes acquiring signal data, including a reflection path signal $V_{RC}$ and an incident path signal $V_{MC}$ via the RF-probe (block 806). The example method 800 of FIG. 8 includes calculating a reflection signal compensated by the incident path signal $V_{MC}$ (block 808). The reflection signal compensated by the incident path signal can be calculated using equation (7), above $$\left(i.e., \rho = \frac{V_{RC}}{V_{MV}} \text{ for } (oc, sc, zo)\right)$$

The example method 800 of FIG. 8 includes calculating the RF-board error correction factors ($E_d$, $E_s$, $E_f$) (block 810). The RF-board error correction factors ($E_d$, $E_s$, $E_f$) can be calculated as follows:

$$E_d = \rho_{zo} \quad (12)$$

$$E_s = \text{Func}_{Es}(\Gamma_{sc}, \Gamma_{oc}; \rho_{sc}, \rho_{oc}, \rho_{zo}) \quad (13)$$

$$E_f = \text{Func}_{Ef}(\Gamma_{sc}, \Gamma_{oc}; \rho_{sc}, \rho_{oc}, \rho_{zo}) \quad (14)$$

The example method 800 includes storing the RF-board error correction factors ($E_d$, $E_s$, $E_f$) for the particular temperature $T_{RF}$ at, for example, a memory in communication with the data processor(s) 216 of FIGS. 2 and 3 (block 812).

The RF-board error correction factors ($E_d$, $E_s$, $E_f$) can be used to calculate the corrected reflection coefficient Γ as discussed in connection with equation (8) and FIG. 7 (e.g., at block 708).

FIG. 9 is a flowchart of an example method 900 to determine the conductivity probe fluids-calibration coefficients (A, B) (i.e., the second set of correction factors) discussed in connection with FIG. 7. The example method 900 of FIG. 9 may be implemented by one or more data processors (e.g., the data processor(s) 216 of FIGS. 2 and 3) located at the surface, downhole, or a combination thereof.

The example method 900 of FIG. 9 includes calculating a brine-water complex-permittivity ε* at a frequency fusing a brine water dielectric model (block 902). For a giving measured brine-water dc-conductivity $\sigma_{dc}$, temperature T, and pressure p, and where s is the salinity of known salt species, the brine-water complex-permittivity ε* can be defined as:

$$\varepsilon = \varepsilon' j\varepsilon'' = \text{func}(s(\sigma_{dc}), T; p)_{f,salt-species} \quad (15)$$

The example method 900 of FIG. 9 includes placing the probe in calibration fluids with known complex permittivities (block 904). For example, the probe can be placed in a reference fluid (e.g., dry air) having a complex-permittivity $\varepsilon_{ref}$, fresh water having a complex permittivity $\varepsilon_1$, and brine water having a complex-permittivity $\varepsilon_2$.

The example method 900 of FIG. 9 includes stabilizing the RF-board (including one or more measurement electronics) at a temperature $T_{RF}$ (block 906). The example method 900 of FIG. 9 includes measuring RF-probe flow mixture data at a frequency f (block 908). Measuring the RF-probe flow mixture data can include, for instance, acquiring a reflection path signal $V_{RC}$ and an incident path signal $V_{MC}$. The example method 900 includes calculating a compensated reflection signal p (block 910). The compensated reflection signal p can be calculated using equation (7), above.

The example method 900 of FIG. 9 includes applying the RF-board correction factors ($E_d$, $E_s$, $E_f$) at TRF to calculate a corrected reflection-coefficient Γ (block 912). The corrected reflection-coefficient Γ can be calculated using equation (8), above.

The example method 900 of FIG. 9 includes measuring the probe's corrected reflection coefficients ($\Gamma_{ref}$, $\Gamma_1$, $\Gamma_2$) (block 914). The example method 900 of FIG. 9 includes calculating the probe's fluids-calibration coefficients (A, B) (block 916). The fluids-calibration coefficients (A, B) can be defined as:

$$G_1 = \frac{\Gamma_{ref} - \Gamma_1}{\Gamma_{ref} + \Gamma_1} \qquad (16)$$

$$G_2 = \frac{\Gamma_{ref} - \Gamma_2}{\Gamma_{ref} + \Gamma_2} \qquad (17)$$

$$A = Func_A(\varepsilon_1, \varepsilon_2, \varepsilon_{ref}; G_1, G_2) \qquad (18)$$

$$B = Func_B(\varepsilon_1, \varepsilon_2, \varepsilon_{ref}; G_1, G_2) \qquad (19)$$

The example method 900 includes storing the probe's calibration data ($\Gamma_{ref}$, $\varepsilon_{ref}$) and the fluids-calibration coefficients (A, B) at, for example, a memory in communication with the data processor(s) 216 of FIGS. 2 and 3 (block 918).

The fluids-calibration coefficients (A, B) can be used to calculate the flow-mixture complex permittivity as discussed in connection with equation (10) and FIG. 7 (e.g., at block 710).

The flowcharts of FIGS. 7-9 are representative of example machine readable instructions that may be used to implement the example conductivity probe systems 200, 300, 400, 500 of FIGS. 2-5. The machine readable instructions may be a program or portion of a program for execution by a processor such as the processor 1012 shown in the example processor platform 1000 discussed below in connection with FIG. 10. The program may be embodied in software stored on a non-transitory computer readable storage medium such as a CD-ROM, a floppy disk, a hard drive, a DVD, a Blu-ray disk, or a memory associated with the processor 1012, but the entire program and/or parts thereof could alternatively be executed by a device other than the processor 1012 and/or embodied in firmware or dedicated hardware. Further, although the example program is described with reference to the flowcharts illustrated in FIGS. 7-9, many other methods of implementing the example conductivity probe systems 200, 300, 400, 500 of FIGS. 2-5 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

As mentioned above, the example processes of FIGS. 7-9 may be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, and (6) B with C.

Figure 10:
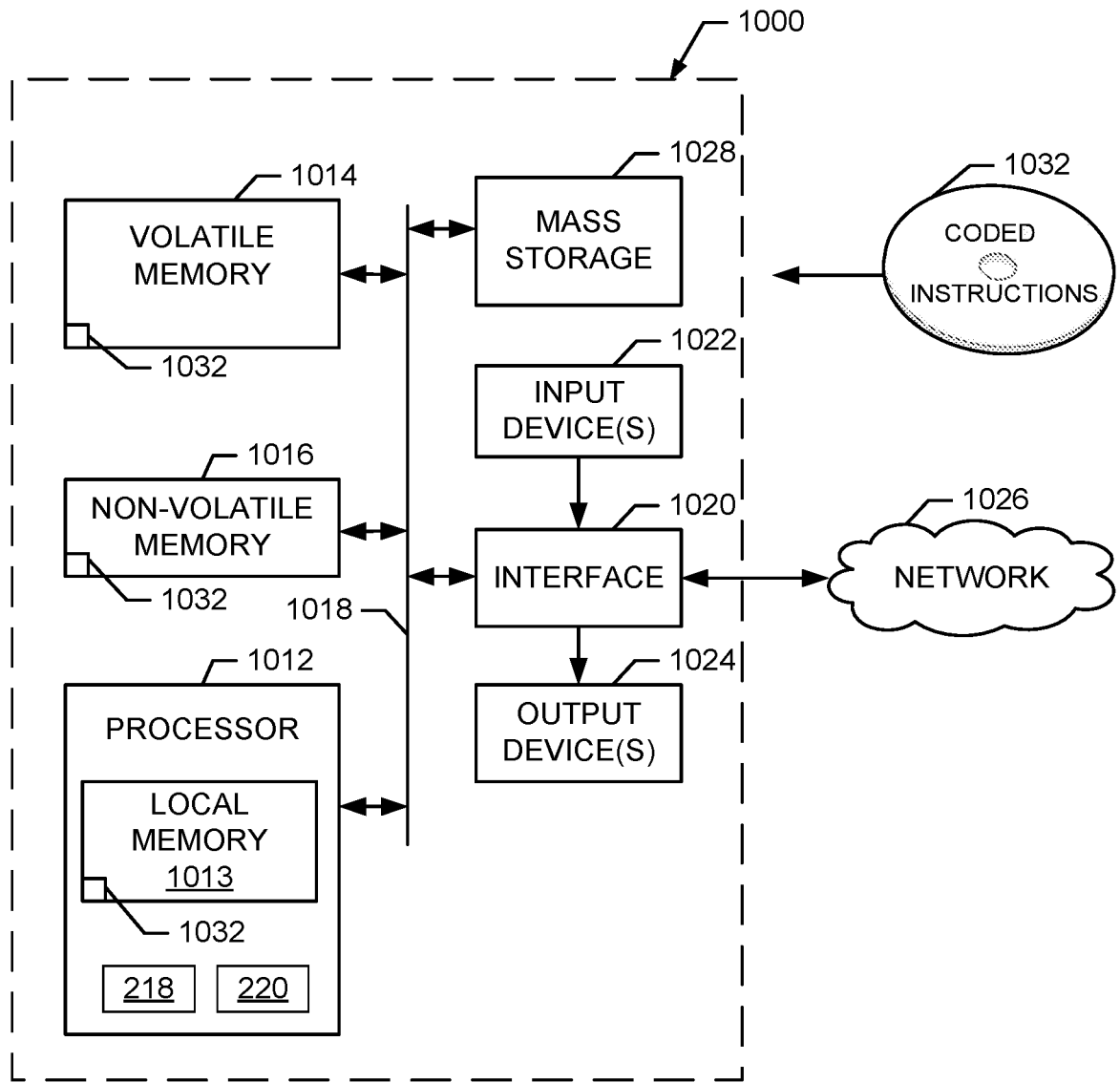
FIG. 10 is a diagram of a processor platform that may be used to carry out the example methods of FIGS. 7, 8, and/or 9 and/or, more generally, to implement the example systems of FIGS. 2-5.

FIG. 10 is a block diagram of an example processor platform 1000 capable of executing instructions to implement the methods of FIGS. 7, 8, and/or 9 to implement the data processor 216 of FIGS. 2 and 3. The processor platform 1000 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, or any other type of computing device.

The processor platform 1000 of the illustrated example includes a processor 1012. The processor 1012 of the illustrated example is hardware. For example, the processor 1012 can be implemented by one or more integrated circuits, logic circuits, microprocessors, GPUs, DSPs, or controllers from any desired family or manufacturer. The hardware processor may be a semiconductor based (e.g., silicon based) device. In this example, the processor implements the probe data analyzer 218 and the MPFM data analyzer 220.

The processor 1012 of the illustrated example includes a local memory 1013 (e.g., a cache). The processor 1012 of the illustrated example is in communication with a main memory including a volatile memory 1014 and a non-volatile memory 1016 via a bus 1018. The volatile memory 1014 may be implemented by Synchronous Dynamic Random Access Memory (SDRAM), Dynamic Random Access Memory (DRAM), RAMBUS® Dynamic Random Access Memory (RDRAM®) and/or any other type of random access memory device. The non-volatile memory 1016 may be implemented by flash memory and/or any other desired type of memory device. Access to the main memory 1014, 1016 is controlled by a memory controller.

The processor platform 1000 of the illustrated example also includes an interface circuit 1020. The interface circuit 1020 may be implemented by any type of interface standard, such as an Ethernet interface, a universal serial bus (USB), a Bluetooth® interface, a near field communication (NFC) interface, and/or a PCI express interface.

In the illustrated example, one or more input devices 1022 are connected to the interface circuit 1020. The input device(s) 1022 permit(s) a user to enter data and/or commands into the processor 1012. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1024 are also connected to the interface circuit 1020 of the illustrated example. The output devices 1024 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), a tactile output device, a printer and/or speaker. The interface circuit 1020 of the illustrated example, thus, typically includes a graphics driver card, a graphics driver chip and/or a graphics driver processor.

The interface circuit 1020 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1026. The communication can be via, for example, an Ethernet connection, a digital subscriber line (DSL) connection, a telephone line connection, a coaxial cable system, a satellite system, a line-of-site wireless system, a cellular telephone system, etc.

The processor platform 1000 of the illustrated example also includes one or more mass storage devices 1028 for storing software and/or data. Examples of such mass storage devices 1028 include floppy disk drives, hard drive disks, compact disk drives, Blu-ray disk drives, redundant array of independent disks (RAID) systems, and digital versatile disk (DVD) drives.

Coded instructions 1032 of FIG. 10 may be stored in the mass storage device 1028, in the volatile memory 1014, in the non-volatile memory 1016, and/or on a removable non-transitory computer readable storage medium such as a CD or DVD.

From the foregoing, it will be appreciated that the above-disclosed apparatus, systems and methods provide for monitoring of conductivity and salinity of water in a multiphase fluid via a conductivity probe. In examples disclosed herein, the conductivity data is used to correct and/or adjust fluid flow data generated based on measurements collected by a fluid flow meter (e.g., a multiphase flow meter) to provide for improved accuracy in, for example, fluid phase holdups and flow rates determined based on the flow meter data, to detect solids in the fluid, etc. Some examples disclosed herein identify changes in reservoir properties based on salinity-vs-time data collected via the conductivity probe. In examples disclosed herein, the need for manual sampling and/or post-processing analysis to account for changes in water salinity in connection with data collected by the flow meter is substantially eliminated. Examples disclosed herein provide for efficient monitoring of water conductivity properties and automatic adjustment of fluid flow data based on the monitoring.

Although the preceding description has been described herein with reference to particular means, materials and embodiments, it is not intended to be limited to the particulars disclosed herein; rather, it extends to all functionally equivalent structures, methods, and uses, such as are within the scope of the appended claims.

What is claimed is:

1. An apparatus comprising:
a flow meter;
a fluid conduit to provide a flow path for a fluid relative to the flow meter;
a conductivity probe coupled to the fluid conduit to generate brine conductivity data of the fluid during flow of the fluid through the fluid conduit; and
a processor, the flow meter and the conductivity probe to be communicatively coupled to the processor, the processor to modify fluid flow data generated by the flow meter based on the brine conductivity data;
wherein the processor is to detect a presence of solid slugs in the flow path of the fluid conduit based on the brine conductivity data, wherein the solid slugs comprise sand.

2. The apparatus of claim 1, wherein the conductivity probe is coupled to the fluid conduit upstream of the flow meter or downstream of the flow meter.

3. The apparatus of claim 1, wherein the processor is to modify the fluid flow data by modifying a gamma-ray water attenuation coefficient based on a brine salinity value derived from the brine conductivity data.

4. The apparatus of claim 1, wherein the conductivity probe is a radio frequency probe.

5. The apparatus of claim 1, wherein the processor is to determine a bottom-hole pressure based on a change in a brine salinity value of the fluid derived from the brine conductivity data.

6. The apparatus of claim 1, wherein the processor is to detect a change in a brine salinity value of the fluid over time based on the brine conductivity data, and wherein the processor is to identify a change in reservoir fluid chemistry based on the detection of the change in the brine salinity value.

7. A method comprising:
generating brine conductivity data by a conductivity probe during flow of a multiphase fluid through a conduit coupled to a flow meter based on a first set of correction factors and a second set of correction factors for the conductivity probe;
applying a correction to fluid flow data generated by the flow meter during flow of the multiphase fluid through the flow meter to generate corrected fluid flow data, the correction based on the brine conductivity data;
determining one or more of a holdup or a flow rate of a phase of the multiphase fluid based on the corrected fluid flow data;
detecting a change in salinity over time based on the brine conductivity data and identifying a change in reservoir fluid chemistry based on the detection; and
identifying a presence of a solid slug in the multiphase fluid flowing through the conduit based on the corrected fluid flow data, wherein the solid slug comprises sand.

8. The method of claim 7, further including calculating a brine-water salinity value from a complex-permittivity value of the multiphase fluid determined by the conductivity probe, wherein the applying of the correction is further based on the brine-water salinity value.

9. The method of claim 7, wherein applying the correction to the fluid flow data includes modifying a gamma-ray water attenuation coefficient.

10. The method of claim 7, further including accessing pressure data and temperature data for the multiphase fluid and calculating a brine salinity value based on the pressure data and the temperature data.

11. The method of claim 7, wherein determining one or more of the holdup or the flow rate of the phase of the multiphase fluid based on the corrected fluid flow data includes determining the holdup of the phase of the multiphase fluid.

12. A method comprising:
applying a correction to fluid flow data generated by a flow meter during flow of a multiphase fluid through the flow meter to generate corrected fluid flow data, the correction based on brine conductivity data generated by a conductivity probe during flow of the multiphase fluid through a conduit coupled to the flow meter;
determining one or more of a holdup or a flow rate of a phase of the multiphase fluid based on the corrected fluid flow data;
identifying a presence of a solid slug in the multiphase fluid flowing through the conduit based on the corrected fluid flow data, wherein the solid slug comprises sand;
detecting a change in salinity over time based on the brine conductivity data by determining a change in slope of the salinity versus square root of the time ($T^{1/2}$); and identifying a change in reservoir fluid chemistry based on the detection.

13. The method of claim 12, wherein detecting the change in salinity over time is or comprises detecting the change in salinity during flowback.

14. The method of claim 12, wherein determining one or more of the holdup or the flow rate of the phase of the multiphase fluid based on the corrected fluid flow data includes determining the holdup of the phase of the multiphase fluid.

15. The method of claim 12, further comprising updating a density of a brine in the multiphase fluid based on the detected change in salinity; and determining a bottom-hole pressure based on the updated density of the brine.

16. A method comprising:
applying a correction to fluid flow data generated by a flow meter during flow of a multiphase fluid through the flow meter to generate corrected fluid flow data, the correction based on brine conductivity data generated by a conductivity probe during flow of the multiphase fluid through a conduit coupled to the flow meter;
determining one or more of a holdup or a flow rate of a phase of the multiphase fluid based on the corrected fluid flow data;
identifying a presence of a solid slug in the multiphase fluid flowing through the conduit based on the corrected fluid flow data, wherein the solid slug comprises sand;
detecting a change in salinity over time during flowback based on the brine conductivity data; and
identifying a change in reservoir fluid chemistry based on the detection.

17. The method of claim 16, further including generating the brine conductivity data based on a first set of correction factors and a second set of correction factors for the conductivity probe.

18. The method of claim 16, wherein determining one or more of the holdup or the flow rate of the phase of the multiphase fluid based on the corrected fluid flow data includes determining the holdup of the phase of the multiphase fluid.

19. The method of claim 16, further comprising updating a density of a brine in the multiphase fluid based on the detected change in salinity; and determining a bottom-hole pressure based on the updated density of the brine.

* * * * *